US010052216B2

(12) United States Patent
Moyer et al.

(10) Patent No.: US 10,052,216 B2
(45) Date of Patent: *Aug. 21, 2018

(54) ONE MOTOR FINGER MECHANISM

(71) Applicant: HDT Expeditionary Systems, Inc., Solon, OH (US)

(72) Inventors: Thomas Moyer, Salt Lake City, UT (US); Eric L. Faulring, Albuquerque, NM (US); Julio J. Santos-Munne, Glenview, IL (US)

(73) Assignee: HDT Expeditionary Systems, Inc., Solon, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/968,271

(22) Filed: Dec. 14, 2015

(65) Prior Publication Data
US 2016/0135967 A1 May 19, 2016

Related U.S. Application Data

(60) Division of application No. 13/925,054, filed on Jun. 24, 2013, now Pat. No. 9,211,200, which is a continuation of application No. 12/965,362, filed on Dec. 10, 2010, now Pat. No. 8,470,051.

(60) Provisional application No. 61/286,345, filed on Dec. 14, 2009.

(51) Int. Cl.
*A61F 2/58* (2006.01)
*A61F 2/50* (2006.01)

(52) U.S. Cl.
CPC ...... *A61F 2/586* (2013.01); *A61F 2002/5072* (2013.01)

(58) Field of Classification Search
CPC ............ A61F 2/583; A61F 2/586; A61F 2/58
See application file for complete search history.

(56) References Cited

U.S. PATENT DOCUMENTS

| 2,002,585 A | 5/1935 | Rothwell, Jr. et al. |
| 2,656,545 A | 10/1953 | Conzelman, Jr. et al. |
| 3,751,733 A | 8/1973 | Fletcher et al. |
| 4,808,187 A | 2/1989 | Patterson et al. |
| 4,834,443 A | 5/1989 | Crowder et al. |
| 5,200,679 A | 4/1993 | Graham |

(Continued)

FOREIGN PATENT DOCUMENTS

| JP | 2006-281380 | 10/2006 |
| JP | 2009-233790 | 10/2009 |

(Continued)

OTHER PUBLICATIONS

International Preliminary Report on Patentability dated Jun. 19, 2012 for International Application No. PCT/US2010/059914.

(Continued)

*Primary Examiner* — Bruce E Snow
(74) *Attorney, Agent, or Firm* — Fay Sharpe LLP

(57) ABSTRACT

A mechanical finger comprises a plurality of phalanges coupled to a single actuator using a kinematic linkage and a differential linkage arranged in parallel. The mechanical finger is capable of exhibiting consistent predictable motion when moving in free space or when contacting an object at the fingertip, and of curling in order to conform to an object when the contact is at other locations on the finger.

13 Claims, 8 Drawing Sheets

(56) References Cited

U.S. PATENT DOCUMENTS

| | | | |
|---|---|---|---|
| 5,246,463 | A | 9/1993 | Giampapa |
| 5,261,266 | A | 11/1993 | Lorenz et al. |
| 5,413,611 | A | 5/1995 | Haslam, II et al. |
| 5,762,390 | A | 6/1998 | Gosselin et al. |
| 5,888,213 | A | 3/1999 | Sears et al. |
| 5,923,139 | A | 7/1999 | Colgate et al. |
| 5,952,796 | A | 9/1999 | Colgate et al. |
| 6,244,644 | B1 | 6/2001 | Lovchik et al. |
| 6,471,618 | B2 | 10/2002 | Pavlov et al. |
| 6,500,210 | B1 | 12/2002 | Sabolich et al. |
| 6,686,911 | B1 | 2/2004 | Levin et al. |
| 6,896,704 | B1 * | 5/2005 | Higuchi .............. A61F 2/583 623/25 |
| 7,222,904 | B2 * | 5/2007 | Matsuda ............ B25J 15/0009 294/106 |
| 7,302,296 | B1 | 10/2007 | Hoffer |
| 7,438,724 | B2 | 10/2008 | Sears et al. |
| 8,470,051 | B2 * | 6/2013 | Moyer ................ A61F 2/586 623/64 |
| 9,211,200 | B2 * | 12/2015 | Moyer ................ A61F 2/586 |
| 2005/0021154 | A1 | 1/2005 | Brimalm |
| 2005/0192676 | A1 | 9/2005 | Sears et al. |
| 2006/0012197 | A1 | 1/2006 | Anderson et al. |
| 2007/0038311 | A1 | 2/2007 | Kuiken et al. |
| 2007/0255424 | A1 | 11/2007 | Leydet et al. |
| 2008/0081728 | A1 | 4/2008 | Faulring et al. |
| 2008/0200994 | A1 | 8/2008 | Colgate et al. |
| 2010/0191343 | A1 | 7/2010 | Puchhammer et al. |

FOREIGN PATENT DOCUMENTS

| | | |
|---|---|---|
| KR | 10-0637956 | 10/2006 |
| WO | WO 2008/092695 | 8/2008 |
| WO | WO 2008092695 A1 * | 8/2008 |
| WO | WO 2009/107164 | 9/2009 |

OTHER PUBLICATIONS

Supplemental Partial European Search Report of European Application No. 10841486.3 dated May 21, 2014, 6 pages.

Book, Wayne et al. (1996) *The concept and implementation of a passive trajectory enhancing robot*, International Mechanical Engineering Congress and Exposition, ASME.

Colgate, J. Edward et al. (1994), *Factors Affecting the Z-Width of a Haptic Display*, IEEE International Conference on Robotics & Automation, pp. 3205-3210, San Diego, CA.

Colgate, J. Edward et al., *Nonholonomic Haptic Display Nonholonomic Haptic Display*, Proceedings of the IEEE 1996 International Conference on Robotics and Automation, Philadelphia, PA.

Faulring, Eric L. et al. (2004), *A High Performance 6-DOF Haptic Cobot*, IEEE International Conference on Robotics and Automation.

Faulring, Eric L. et al. (2005) *High Performance Cobotics*, IEEE $9^{th}$ International Conference on Rehabilitation Robotics, Jun. 26, 2005.

Gillespie, R.B. et al. (2001) *A General Framework for Cobot Control*, IEEE Transactions on Robotics and Automation, 17(4) p. 391, Aug. 2001.

Moore, Carl et al. (2003) *Cobot Implementation of Virtual Paths and 3D Virtual Surfaces*, IEEE Transactions on Robotics and Automation, 19(2), p. 357-351, Apr. 2003.

Peshkin, Michael A. et al. (2001) *Cobot Architecture*, IEEE Transactions on Robotics and Automation, 17(4), p. 377, Aug. 2001.

Gillespie, R. Brent et al., *Kinematic Creep in a Continuously Variable Transmission: Traction Drive for Mechanics for Cobots*, Journal of Mechanical Design, Dec. 2002, vol. 124, p. 713-722.

Moore, Carl A. et al., *Design of a 3R Cobot Using Continuously Variable Transmissions*, 1999 International Conference on Robotics and Automation, Detroit, MI.

Paula, Greg, *Cobots for the assembly line*, 1997 American Society of Mechanical Engineers, 7 pages.

Moore, Jr., Carl A., *Continuously Variable Transmission for Serial Link Cobot Architecture*, Degree of Masters of Science in Mechanical Engineering, Northwestern University, Mar. 17, 1997, 91 pages.

Singer, Emily, *A Prosthetic Arm That Acts Like a Real One*, Technology Review, Nov. 27, 2007 (3 pages).

Singer, Emily, *Prosthetic Limbs That Can Feel*, Technology Review, Nov. 27, 2007 (2 pages).

Jeffrey, Susan, *Targeted Muscle Reinnervation Improves Use of Prosthetic Arm*, Medscape Medical News, Feb. 8, 2007 (4 pages).

Kuiken, T.A. et al., *The use of targeted muscle reinnervation for improved myoelectric prosthesis control in a bilateral shoulder disarticulation amputee*, a research paper for submission to Prosthetics and Orthotics International, 2004 (16 pages).

\* cited by examiner

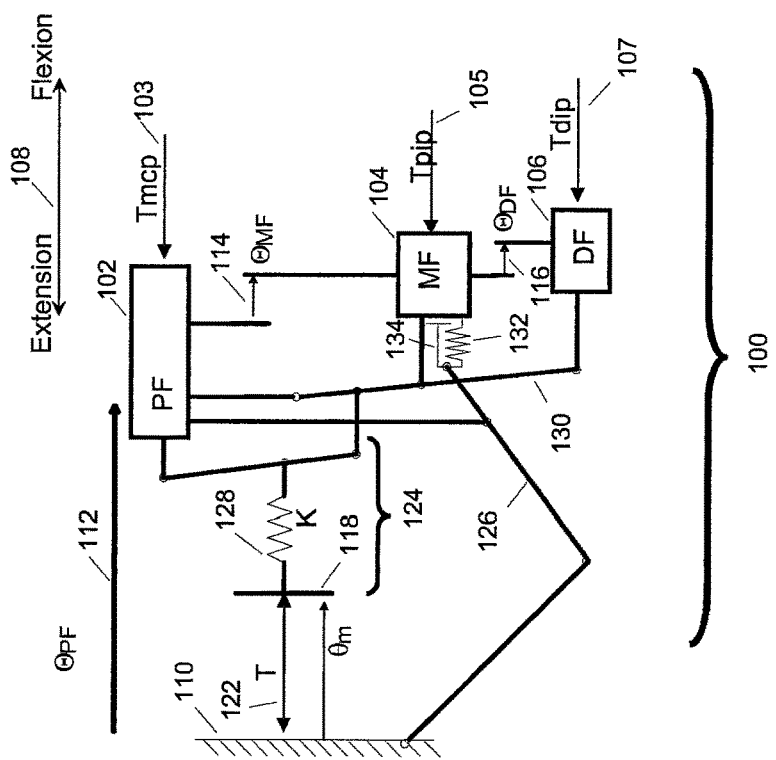
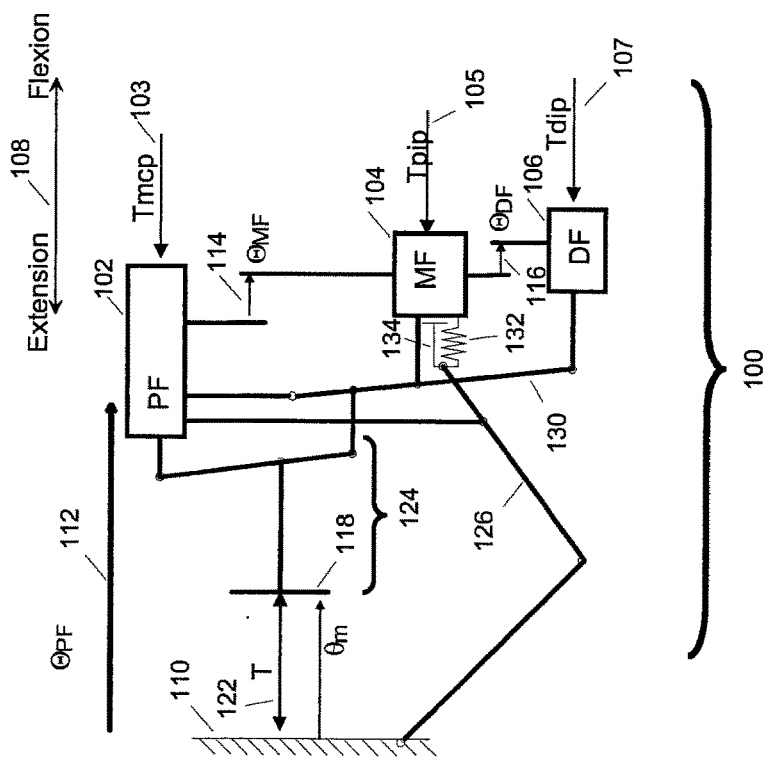
Fig. 1B
Fig. 1A

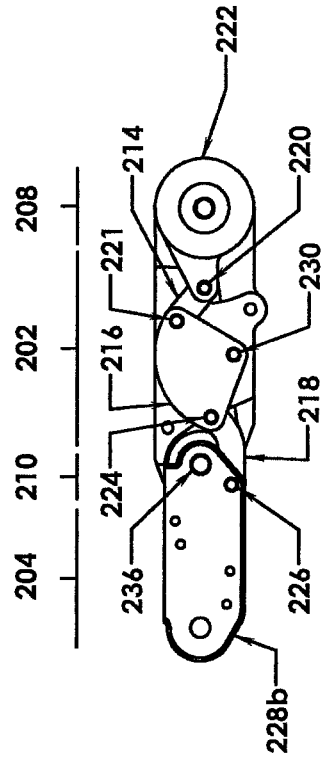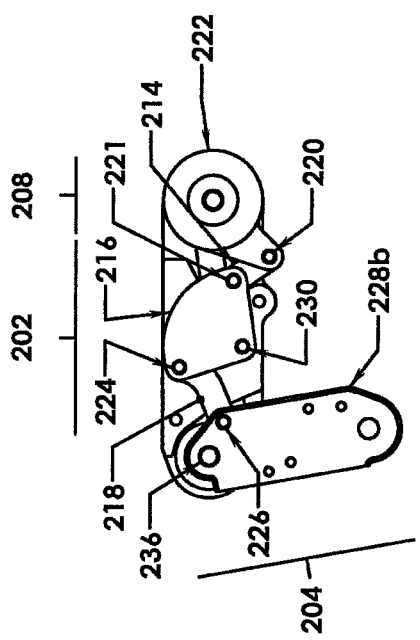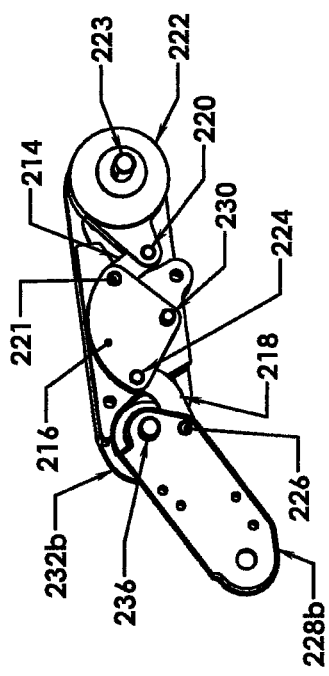

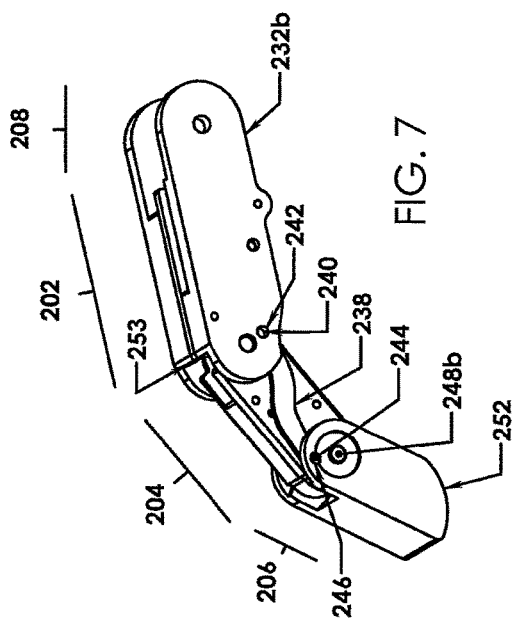
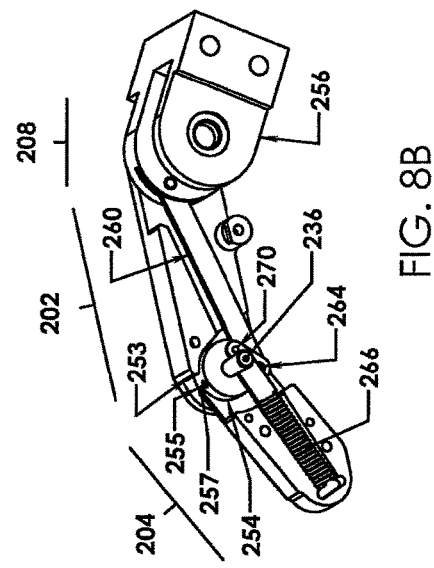
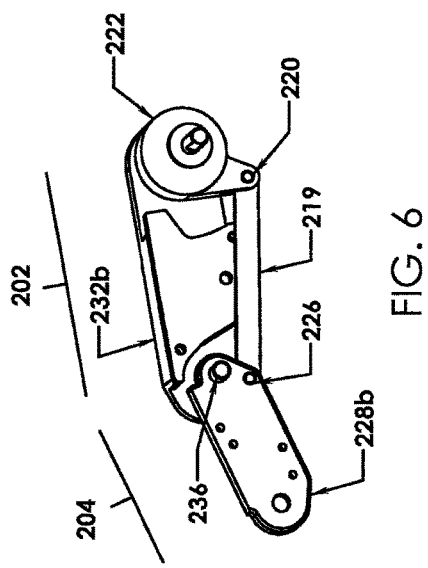
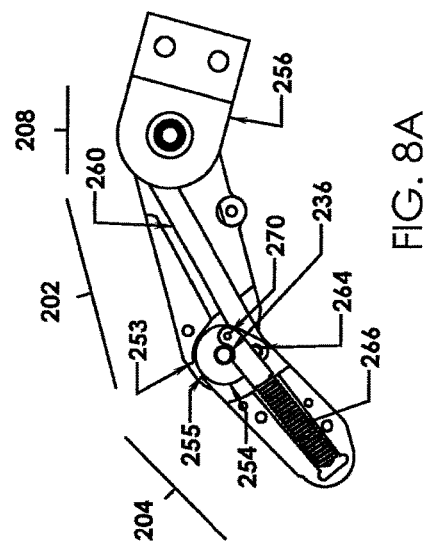

ONE MOTOR FINGER MECHANISM

CROSS-REFERENCE TO RELATED APPLICATIONS

This application is a divisional of U.S. application Ser. No. 13/925,054 filed Jun. 24, 2013, now assigned U.S. Pat. No. 9,211,200, which is a continuation of U.S. application Ser. No. 12/965,362 filed Dec. 10, 2010, now U.S. Pat. No. 8,470,051, which claims priority from and benefit of the filing date of U.S. provisional application Ser. No. 61/286,345 filed Dec. 14, 2009, and the entire disclosure of each of said prior applications is hereby expressly incorporated by reference into the present specification.

GOVERNMENT INTEREST

This invention was made with government support under Contract No. N66001-06-C8005, awarded by Defense Advanced Research Projects Agency. The government has certain rights in the invention.

BACKGROUND

A "mechanical finger" refers to an elongated, articulating, mechanical appendage. Like a human finger, a mechanical finger has one end joined to a structure that acts as a base and an opposite end that is not anchored or connected. A mechanical finger used for grasping typically has two or more rigid sections, and preferably at least three, connected end to end by articulating joints. Terminology used to describe the anatomy of a human finger is used to describe a mechanical finger. As in the human finger, each section of the finger is referred to as a "phalanx." A finger extends from a base and is comprised of at least two, and preferably three, phalanges joined end to end by pivoting or articulating joints. A first articulating joint joins a proximal phalanx to a base, such as a palm of a hand. A second articulating joint joins the proximal phalanx to an intermediate or middle phalanx, and a third articulating joint joins the intermediate phalanx to a distal phalanx. The first joint is referred to as the metacarpophalangeal (MCP) joint, the second as the proximal interphalangeal (PIP) joint, and the third as the distal interphalengeal (DIP) joint.

In a mechanical finger, the phalanges are coupled to one or more motors to cause flexion and extension of the finger. When using a kinematic mechanism for coupling a single motor to the phalanges, the position of the actuator fully determines the position of the joints, but the torque at each joint is unknown. With a differential mechanism, the torque at the actuator determines the torque at each of the driven joints, but neither the velocity nor the position of the individual joints are specified by the actuator velocity or position alone. A kinematic mechanism produces consistent, predictable motion of the finger joints, but it does not allow the finger to curl around an object. Differential mechanisms allow curling and grasping, but often deviate from the desired motion due to forces at the fingertip, causing buckling, or due to friction in the joints, causing undesirable curling behavior when not conforming.

BRIEF DESCRIPTION

According to one aspect of an exemplary embodiment of a mechanical finger comprising at least two phalanges driven by a single actuator, and a differential transmits torque in parallel from the actuator to the MCP joint and the PIP joint.

According to another aspect, the mechanical finger further includes a variable stop that limits rotation of the PIP joint based on the angle of rotation of the MCP joint. Such a mechanical finger is capable of exhibiting consistent predictable motion when moving in free space or when contacting an object at the fingertip, and curling in order to conform to an object when the contact is at other locations on the finger.

BRIEF DESCRIPTION OF THE DRAWINGS

FIG. 1A is a schematic illustration of a mechanical finger driven by a single actuator.

FIG. 1B is a schematic illustration of an alternate embodiment of a mechanical finger driven by a single actuator.

FIG. 4A is a side view, rendered with perspective, of proximal and medial phalanges of the prosthetic finger of FIG. 2, which is only partially constructed to reveal a differential linkage.

FIG. 4B is a side view, not rendered with perspective, of the partially constructed proximal and medial phalanges of the prosthetic finger of FIG. 2, in an extended position.

FIG. 4C is a side view, not rendered with perspective, of the partially constructed proximal and medial phalanges of the prosthetic finger of FIG. 4B, in a fully flexed position.

FIG. 6 is a side view, rendered in perspective of proximal and medial phalanges of alternate embodiment of a mechanical partially constructed to reveal a differential linkage.

FIG. 7 is a side, perspective view of the partially constructed prosthetic finger of FIG. 2, with certain elements removed to reveal a linkage.

FIG. 8A is a side, non-perspective view of the prosthetic finger of FIG. 2, with several parts removed to illustrate a stop linkage.

FIG. 8B is a perspective view of FIG. 7B.

DETAILED DESCRIPTION

Figure 1D:
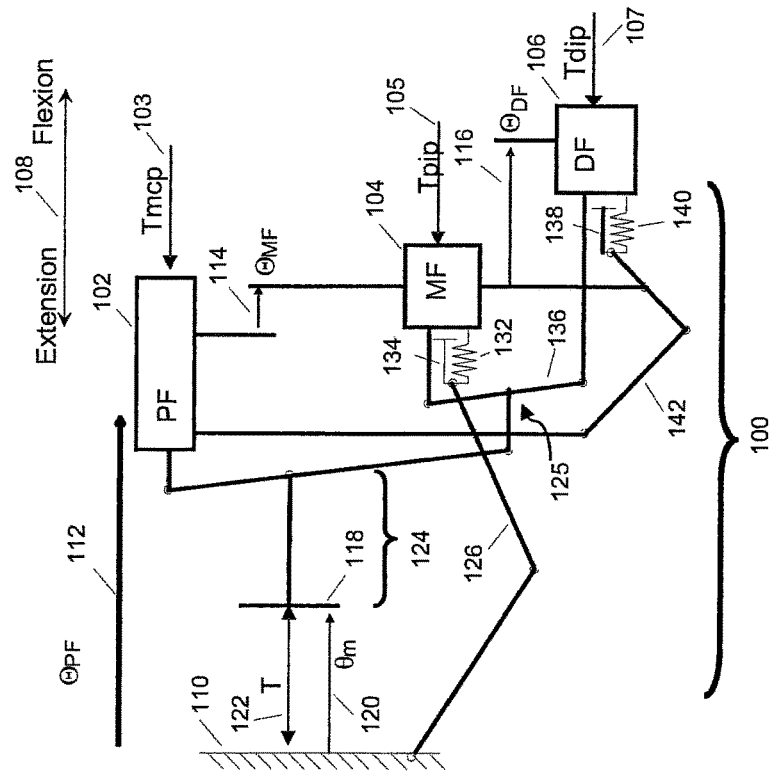
FIG. 1D is a schematic illustration of an alternate embodiment of a mechanical finger driven by a single actuator.
Figure 1C:
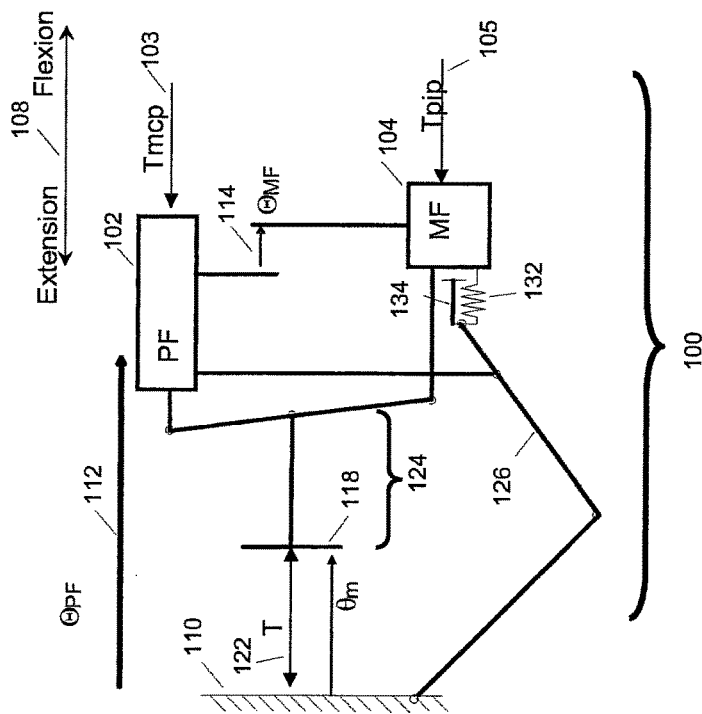
FIG. 1C is a schematic illustration of an alternate embodiment of a mechanical finger driven by a single actuator.

In the following description of a mechanical finger, like numbers refer to like parts.

FIGS. 1A-1E schematically illustrate several alternative embodiments of mechanisms for driving a mechanical finger 100 using a single motor. The mechanism combines a differential, a kinematic linkage and a PIP linkage for coupling the torque and position of a drive output to a mechanical finger 100 having at least two sections in order to control its flexion and extension in a manner that permits it to be used in connection with grasping or other applications in which a curling action is desirable. Such applications include, but are not limited to, robotic hands and prosthetic hands.

The illustrated examples of mechanical finger 100 comprise at least a proximal phalanx 102, a medial or middle phalanx 104, and, in the embodiments of FIGS. 1A to 1E, a distal phalanx 106. "Phalanx" refers to an elongated, rigid section of the finger, and "phalanges" to multiple sections of the finger. The phalanges are sometimes also referred to herein as first, second and third sections, respectively, of the mechanical finger. Articulating joints, which are not expressly indicated in the figure, permit joined phalanges to pivot with respect to each other around an axis of the joint. The X-axis 108 of the figure represents the angle of extension and flexion of the phalanges relative to each other and to a reference ground 110. A greater angle indicates flexion of the finger and a smaller angle indicates extension of the finger. The length of arrow 112 represents the angle, designated by the variable $\Theta_{PF}$ between the proximal phalanx 102 and a ground 110. Similarly, the lengths of arrows 114 and 116 represent the relative angles between the proximal phalanx and the middle phalanx, and between the middle phalanx and the distal phalanx, respectively. These angles are designated in the figure by the variables $\Theta_{MF}$ and $\Theta_N$, respectively.

The angular position and torque transmitted by an output of a single actuator or drive, which output is represented by line 118, controls the flexion and extension of the finger. Any type of suitable motor can power the actuator or drive. The type of the motor will depend on the application. The angular position of the output is represented by line 120 and is designated by the variable $\Theta_m$. Torque applied to an object by a joint is represented as a linear force in the figure. The torque delivered by the output of the drive is represented by line 122. Variable $T_m$ represents the magnitude of the torque from a motor connected to the drive. Note that the motor is not expressly illustrated in the figures. Torque on the metacarpophalangeal (MCP) joint (not shown), designated $T_{mcp}$, which is generated by force applied to the proximal phalanx, is represented by line 103. Similarly, torque on the proximal interphalangeal (PIP) joint (not shown) is designated $T_{pip}$ and is represented by line 105. Torque on the distal interphalangeal (DIP) joint (not shown) is designated $T_{pip}$ and is represented by line 105.

A hybrid mechanism comprising a kinematic linkage and differential enables conformal grasping by the finger due to the differential, but at the same time curling behavior can be precisely defined during application of forces to the distal phalanx only. In the examples illustrated by the schematics of FIGS. 1A-1E, a differential 124 coupled to ground 110 applies the torque $T_m$ from the motor to the proximal phalanx 102. The differential also applies the torque to linkage 130 in the embodiments of FIGS. 1A, 1B, 1D, or to medial phalanx 104 in the two-phalanx embodiment of FIG. 1C, or to a second differential 125 in the embodiment of FIG. 1E. The differential 124 couples the drive output with the MCP joint and the PIP joint. Thus, the drive applies torque to both the PIP and MCP joints in the embodiments of FIGS. 1A-1C and 1E. In the embodiment of FIG. 1D, the combination of differential 124 and differential 125 applies torque applied to the MCP, PIP and DIP joints.

Figure 1E:
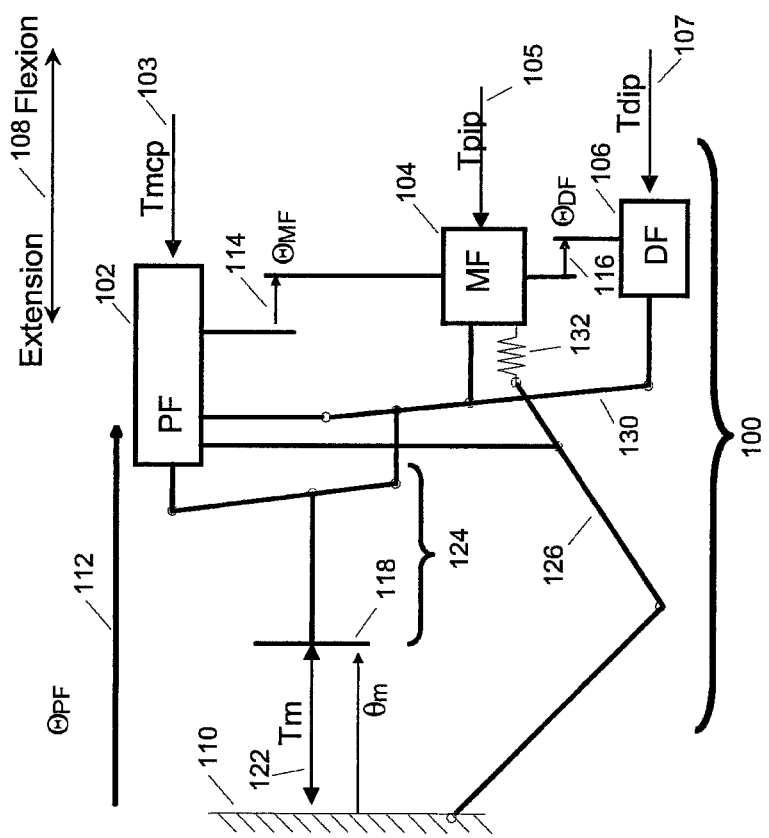
FIG. 1E is a schematic illustration of an alternate embodiment of a mechanical finger driven by a single actuator.

Linkage 130 in FIGS. 1A, 1B, and 1E functions as a kinematic linkage, coupling the motion of PIP and DIP joints through an algebraic relationship. Linkage 130 couples the PIP and DIP joints (not shown), so that both joints rotate together, in a fixed relationship, resulting in the medial and distal phalanges curling together in a natural curling motion. Movement of link 130 relative to the proximal phalanx 102 causes the middle phalanx to rotate about the PIP joint (not shown), and the distal phalanx to rotate with respect to the middle phalanx around the DIP joint (not shown). This coupled curling relative to the proximal phalanx 102 occurs even while motion of proximal phalanx 102 is blocked, such as when conformal grasping is occurring.

As shown in the embodiment illustrated only in FIG. 1B, the linkage 124 may, optionally, include a compliant element 128, in series with ground, represented in the figure by spring 128. The compliant element is, for example, comprised of an elastic element that generates a spring force. The spring provides compliance for series elasticity and shock mitigation by allowing linkage 124 to stretch a little when forces are applied to it. Elasticity and shock mitigation or dampening can be desirable in certain applications, such a prosthetics. Movement of the linkage 130 relative to the proximal phalanx 102, such as during curling when the proximal phalanx 102 is blocked, also results in compression of a compliant member represented in the figure by a spring 132 coupled between the proximal phalanx and the link 130. The spring acts to extend the PIP joint.

Referring only to FIGS. 1A-1D, in each of the illustrated examples a linkage 126 adjusts the position of stop 134 based on rotation of the MCP joint. Stop 134 limits the range of motion of the PIP joint. The linkage sets the position of the hard stop based on the degree of rotation of the MCP joint from ground. Stopping rotation of the PIP joint limits extension of the medial phalanx, as well as the distal phalanx, beyond a predetermined angle relative to the proximal phalanx. The angle of rotation of the MCP joint is represented in the figure as the distance between ground 110 and the proximal phalanx 102. The angle of the PIP joint relative to the phalanx is indicated by the length of line 114 in the figure. The stop rotates with respect to the PIP joint as the MCP joint rotates, and thus it depends on the angle of the MCP joint. When the proximal phalanges motion is not blocked, the stop linkage 126 enforces natural, simultaneous curling of all three joints, the MCP, PIP and DIP joints. Linkage 126 also enables the finger to resist forces on the distal phalanx without the differential allowing the PIP and DIP joints to straighten and the MCP joint to flex. Despite the system having a differential, the posture of all three joints can thus remain fixed (not against stops) irrespective of the magnitude of a single external force applied to the distal phalanx.

Because of the use of a differential linkage to couple torque from the drive to the MCP and PIP joints, the positions of the MCP and PIP joints are not fully determined by the position of the drive. For any given position of the drive output, the finger mechanism has one free motion available, which is an extension of the proximal phalanx and a flexing of the PIP and DIP joints. Preferably, linkage dimensions and moment arms are chosen so that external forces applied to the finger distal to a point near the fingertip act to straighten the finger, and forces applied proximal to this point act to curl the finger. The point at which the behavior changes from straightening to curling is referenced as the "focal point" of the differential. For external forces that act proximal to the focal point, the MCP joint will extend and the PIP joint will flex.

Referring now to FIGS. 1A-1E, the linkage 126 is also used to move the endpoint for return spring 132. The return spring 132 acts to straighten the finger and to keep the mechanism pushed over to one side of this free range of motion. In the absence of any external forces pushing on the finger, the return spring makes the finger act as though the differential 124 is not present. The return spring can also provide some resistance to curling of the fingers when forces are applied to the dorsal side of the finger. Any compliance in the differential 124 will result in some motion, but this will occur in all three joints and is not due to the differential coupling.

As illustrated by the embodiment of FIG. 1E, adjustable stop 134 for the PIP joint may be omitted for an application not requiring it, or in which it is desirable not to have it. In this example, the linkage 126 controls only the position of the end point of the PIP joint return spring 132. The linkage 126 thus becomes a spring centering linkage.

Referring now only to FIG. 1D, this embodiment of a mechanical finger includes a differential 125 comprising differential linkage 136 in place of a kinematic linkage. The differential couples the medial and distal phalanges using a differential relationship. This embodiment also optionally includes an adjustable stop 138 for the DIP joint and return spring 140 for placing a torque on the DIP joint that tends to extend the distal phalanx relative to the medial phalanx. Linkage 142 is connected to proximal phalanx 102 and adjusts the position of DIP stop 138 based on the angle of rotation of the PIP joint. It also sets the endpoint of return spring 140.

FIGS. 2, 3, 4A-4C, 5A-5C, 6, 7 and 8A-B illustrate various aspects of an exemplary embodiments of mechanical finger 100 for use in a prosthetic application. The prosthesis comprises at least one prosthetic finger 200. The prosthesis may also include, depending on the needs of the patient, a prosthetic hand, comprising a prosthetic palm to which the mechanical finger is attached, and a prosthetic arm, to which the prosthetic hand is attached. Only the internal structure of the prosthetic finger is illustrated in the figures.

Prosthetic finger 200 is comprised of proximal phalanx 202, medial phalanx 204, and distal phalanx 206. Distal phalanx 206 has been omitted from FIGS. 4A-4F for purposes of illustration. Metacarpophalangeal (MCP) joint 208 connects the finger to a base element, for example, an artificial palm or hand, which is not shown. Proximal interphalangeal (PIP) joint 210 joins the proximal and medial phalanges. Distal interphalangeal (DIP) joint 212 joins the medial and distal phalanges.

In the embodiment shown in FIGS. 3 and 4A-4C, the proximal phalanx 202 houses a differential linkage comprised of a connecting rod 214, a pivot link 216, and another connecting rod 218. Connecting rod 214 is joined by pin 220 to an arm extending from drive output 222, and thus connects the output drive to one end of the pivot link 216. Although not shown, a motor—a stepper motor, for example—located in the base element rotates a drive input, which in this example is pin 223, which in turn rotates the drive output. Drive output 222 is fixed to the pin 223. Pin 221 joins the connecting rod to the spring. Connecting rod 218 connects the other end of the pivot link to plate 228 of the medial phalanx 204. Pin 224 joins the pivot link to the connecting rod 218, and pin 226 joins the connecting rod to the plates 228a and 228b, which comprise the primary structural elements for medial phalanx 204. The midpoint of the pivot link is fixed by pin 230 to plates 232a and 232b.

The pivot link will rotate within the proximal phalanx, about the axis of pin 230, as indicated by comparing FIGS. 4B and 4C, when the drive output rotates. During flexion, rotation of the drive output 222 pulls the connecting rod 214, which pulls on the pivot link 216, which pulls on a second connecting rod 218, which pulls on plates 228a and 228b of the medial phalanx.

Figure 5A:
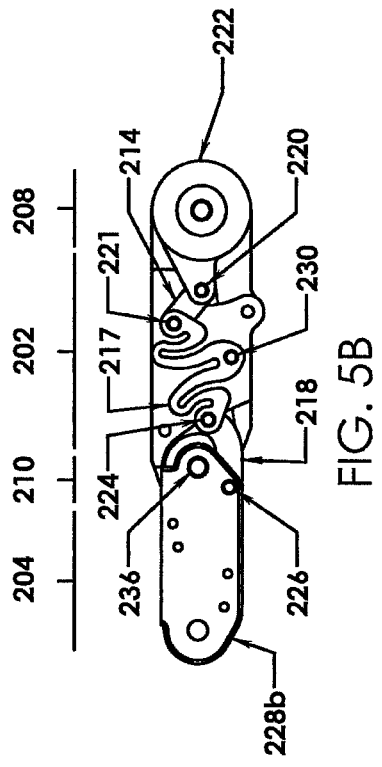
FIG. 5A is a side view, rendered with perspective, of proximal and medial phalanges of an alternate embodiment of a prosthetic finger that is partially constructed to reveal a differential linkage.
Figure 5B:
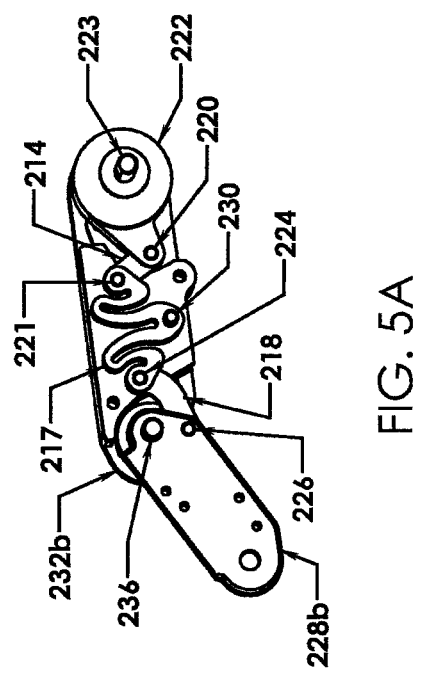
FIG. 5B is a side view, not rendered with perspective, of the partially constructed proximal and medial phalanges of an alternate embodiment of the prosthetic finger of FIG. 2, in an extended position.
Figure 5C:
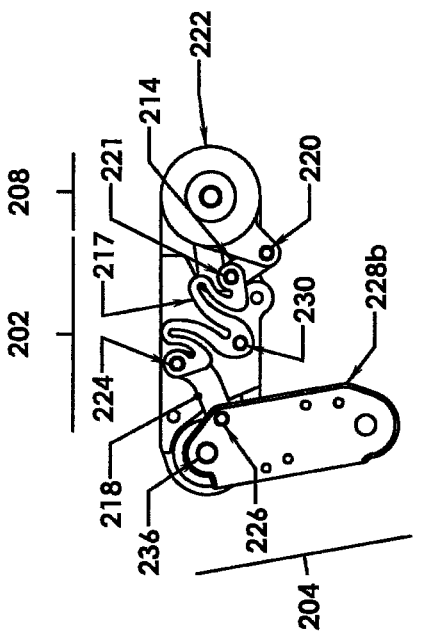
FIG. 5C is a side view, not rendered with perspective, of the partially constructed proximal and medial phalanges of an alternate embodiment of the prosthetic finger of FIG. 5B, in a fully flexed position.

In an alternate embodiment shown in FIGS. 5A-5C, the pivot link 216 (FIGS. 4A-4C) is replaced by an in series compliant element for giving the finger compliance for series elasticity and shock mitigation. In this example, the compliant element comprises spring 217. Except for the added compliance and elasticity provided by the spring, the differential with spring performs in a substantially similar manner as the pivot link 216. In another alternate embodiment shown in FIG. 6, the pivot link 216 and the connecting rods 214 and 218 are replaced with a linkage comprising a single connecting rod 219 that is connected by pins 220 and 226 to the drive housing 220 and plate 228b of the medial phalanx 204. As can be seen in the figure, the connecting rod must extend beyond the envelope of the proximal phalanx 204.

In each of the embodiments shown in FIGS. 2 to 8B, plates 228a and 228b are the primary structural elements of medial phalanx 204. Plates 232a and 232b are the primary structural elements comprising the proximal phalanx 202. The differential linkage of FIGS. 4A-4C and 5A-5C described above is housed between the plates. To these plates can be attached shells to give the proximal phalanx its desired exterior shape in the particular prosthetic or other application.

The pins used to join components in the differential linkage, as well as in other linkages described below, permit relative rotation of the joints that are joined. The location of pin 226 is eccentric to the axis of the PIP joint to form a moment arm. The axis of the PIP joint is defined by pin 236, which pivotally connects the clevis formed by plates 232a and 232b of the proximal phalanx with plates 228a and 228b of the medial phalanx. For a given rotation of the drive output, either the MCP joint or the PIP joint can rotate. Rotation of the drive output not only applies torque to the MCP joint by causing the pivot link to push against pin 230, but it also rotates the link, causing the other part of the link to transmit a force that is applied to pin 226. Even if the proximal phalanx is blocked, the link will nevertheless pivot and apply torque to the PIP joint. Thus, torque from the drive is applied to both the MCP joint and the PIP joint.

Figure 2:
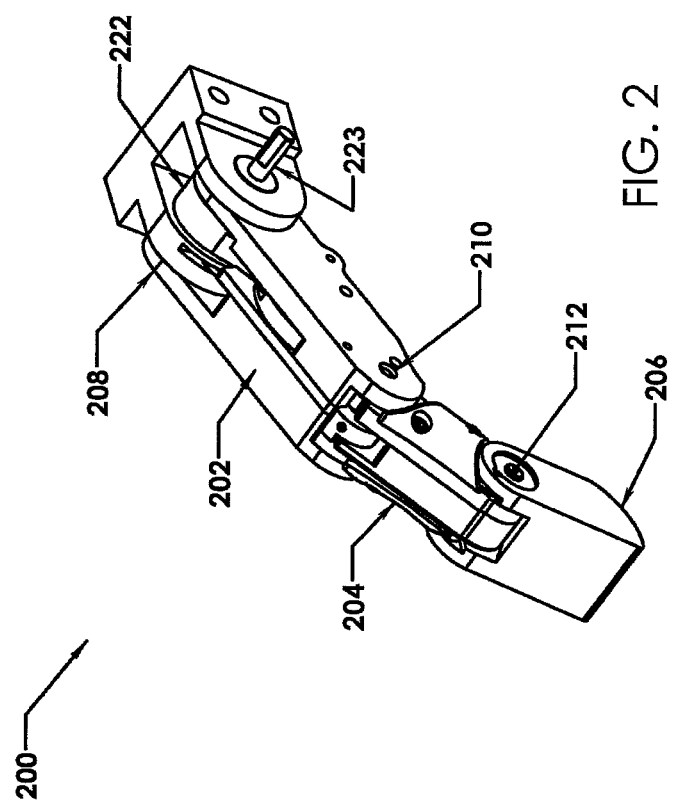
FIG. 2 is a perspective view of an example of a prosthetic finger, partially constructed and without a covering, embodying a coupling mechanism according to the principles of the mechanical finger of FIG. 1.
Figure 3:
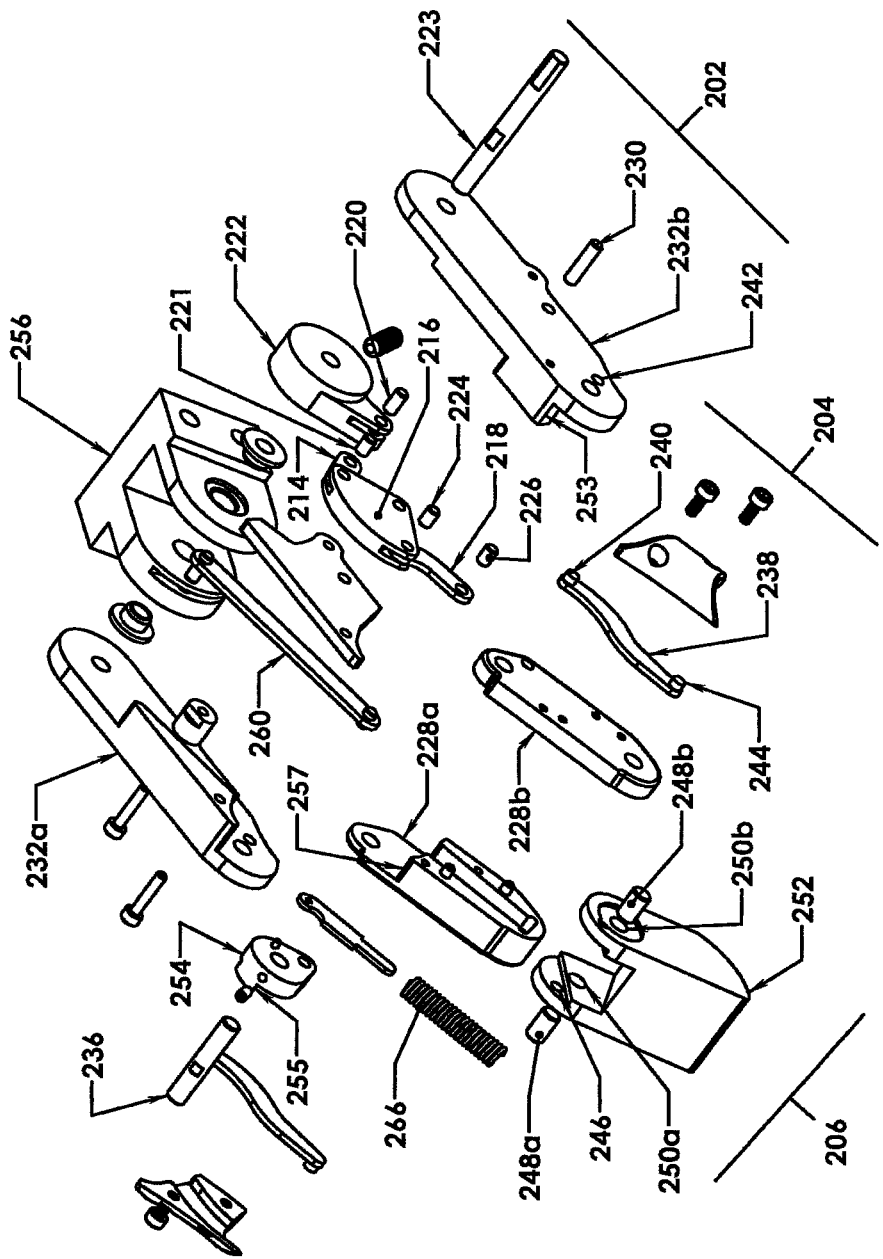
FIG. 3 is an exploded view of the prosthetic finger of FIG. 2.

Referring now to FIGS. 2, 3, and 7, the medial phalange 204 houses a kinematic linkage for coupling rotation of the PIP joint to the DIP joint so that both curl simultaneously. The kinematic linkage comprises a connecting rod 238 that spans between the proximal phalanx 202 and the distal phalanx 206. Pin 240 at a proximal end of the connecting rod engages hole 242 on plate 232b of the proximal phalanx. Pin 244 on the distal end of the connecting rod engages hole 246 in the distal phalanx. The distal phalanx is linked to the medial phalanx by a hinge formed by pins 248a and 248b. These pins cooperate respectively, with a hole 250a on plate 228a and hole 250b on plate 228b of the medial phalanx, and with holes 250a and 250b on opposite forks of a clevis extending from a shell forming distal phalanx 252. Although in this embodiment the linkage is comprised of a single connecting rod, it could comprise multiple links. Furthermore, a differential could be substituted for the kinematic linkage, as described in connection with FIG. 1D.

Referring now only to FIGS. 2, 3, 8A and 8B, the mechanical finger 200 includes, in this embodiment, fixed stop 253 that stops rotation of the PIP joint to prevent hyperextension of the medial phalanx. In this embodiment, a movable PIP stop part 254 rotates on the same axis as the PIP joint to reduce the permitted range of motion of the medial phalanx by limiting further rotation of the PIP joint based on the degree of flexion of the MCP joint. The centerline of pin 236 defines the axis of rotation. The PIP stop part stop includes a stop portion 255 that interferes with 257 of plate 228a of the medial phalanx to prevent the medial phalanx from extending. The position of the PIP stop part 254 is based on the degree of rotation of the MCP joint, and is accomplished in this embodiment by a linkage comprising connecting rod 260 between a housing 256 for a drive (not shown) and PIP stop part 254. The linkage may also be implemented using multiple links. A pin connects the distal end of connecting rod 260 to arm portion 264 of the PIP stop part 254. The proximal end of connecting rod 258 is connected by another pin to the drive housing. As the MCP joint rotates due to flexion of the proximal phalanx 202, the connecting rod pulls on the arm 264, causing the PIP stop part to rotate in the same direction.

With the PIP-stop linkage, the medial phalanx 204 is stopped either by the fixed stop 253 on the proximal phalanx when the proximal phalanx is fully extended, or by the movable stop of PIP-stop part 254 when the MCP joint is rotated during flexion of the proximal phalanx. If the MCP joint rotates, then the PIP joint is forced to rotate as well by the PIP-stop part. During free motion, or when forces are applied to the fingertip, movement of the PIP-stop part helps to produce predictable curling like a fully kinematic mechanism.

In this embodiment, the rotational position of the PIP-stop part 254 also controls the endpoint 270 of the return spring 266. This spring, which is normally compressed, has the effect of extending the medial phalanx, thus pushing the PIP joint against the PIP-stop. If no external forces act on the finger, the force generated by the spring causes the motion of the finger joints to be controlled by the PIP-stop. If, however, an object blocks the motion of the proximal phalanx, then the differential linkage continues applying torque to the PIP joint, causing PIP and DIP joints to curl and further compressing the return spring.

The kinematic linkage for controlling the position of the PIP stop based on the motion of the MCP joint could also be used to limit or affect the motion of the PIP and DIP joints in other ways. For example, the PIP stop can be removed, permitting the linkage to be for controlling the end point of the return spring without limiting the motion of the PIP joint.

Although not necessary for operation of the finger as described above, joint positions can be measured using potentiometers coupled with the joints and feedback to a controller for the drive motor in order to drive the finger to desired position, subject to the limitations of being able to do so caused by the differential. Similarly, strain gauges can be placed on, for example, the drive housing 256 to measure torque on the finger and feed the measured torque back to a controller to change the impedance of the finger.

Although the particular components forming the linkages and the phalanges illustrated in FIGS. 2-7 have advantages when used in a prosthetic application, the structures are intended to be illustrative only of the linkage mechanisms illustrated by FIG. 1. These components can be adapted or substituted for when implementing a differential mechanism in parallel with a kinematic mechanism in accordance with FIG. 1. For example, linkages may be replaced with belts or cables or other passive mechanical mechanisms to achieve the same general purpose. Although it is common to use linkages for kinematic mechanisms and cables for differential mechanisms, but either type can be used for either purpose. In addition to being implemented as a linkage, as exemplified by FIGS. 2-8B, the differentials described above may also be implemented using a belt or cable, for example one linking the drive output to a drum or pulley at the PIP joint, a gear train, or a toggle.

Furthermore, applications in which a mechanical finger in accordance with FIGS. 1A-1E can be used include any type of application involving grasping, and include many different types of robotic applications that are not limited to those attempting to mimic a human hand or prosthetic applications. For instance, an anthropomorphic grip may have benefits in many diverse or unstructured or unforeseen contexts just as human hands are so successfully versatile, including industrial grippers, rovers or mobile robots, entertainment, home robots, surgery or minimally invasive surgery, massage, patient transfer or stabilization, and many others.

The foregoing description is of exemplary and preferred embodiments. The invention, as defined by the appended claims, is not limited to the described embodiments. Alterations and modifications to the disclosed embodiments may be made without departing from the invention. The meaning of the terms used in the claims are, unless expressly stated otherwise, intended to have ordinary and customary meaning and are not intended to be limited to the details of the illustrated structures or the disclosed embodiments.

The invention claimed is:

1. A mechanical finger comprising:
a proximal phalanx and a medial phalanx, the proximal phalanx coupled between a first and a second joint;
the first joint being adapted for coupling to an associated base element to permit articulation of the proximal phalanx with respect to the associated base element;
a differential linkage adapted for receiving torque from an associated drive output and for transmitting torque to both the proximal and medial phalanx, said differential linkage comprising a pivot link pivotally connected to said proximal phalanx;
said differential linkage further comprising first and second connecting rods pivotally connected to said pivot link, wherein said first connecting rod is located at a one end of said pivot link and is adapted for connection to the associated drive output and wherein said second connecting rod is located at another end of said pivot link and is pivotally connected to a primary structural element of said medial phalanx;
said mechanical finger further comprising a third joint and a distal phalanx coupled to the third joint, the medial phalanx being coupled between the second joint and the third joint.

2. The mechanical finger of claim 1, further comprising a spring for placing a torque on the second joint in a direction that forces the medial phalanx to extend with respect to the proximal phalanx.

3. The mechanical finger of claim 1, wherein the pivot link of the differential comprises a pivoting compliant link for transmitting torque to both the proximal and medial phalanx, said pivoting compliant link comprising a spring that provides series elasticity and shock mitigation.

4. The mechanical finger of claim 1, further comprising a kinematic linkage for coupling rotation of the second and third joints.

5. The mechanical finger of claim 1, further comprising a differential linkage for coupling the second and third joints.

6. An apparatus comprising:
a proximal phalanx, a medial phalanx, and a distal phalanx;
a MCP joint connected to a first end of said proximal phalanx and adapted for coupling to an associated base element to permit articulation of the proximal phalanx with respect to the associated base element;
a PIP joint connected to a second end of said proximal phalanx and connected to a first end of said medial phalanx, said PIP joint permitting articulation of said medial phalanx relative to said proximal phalanx;
a DIP joint connected to a second end of said medial phalanx and connected to a first end of said distal phalanx, said DIP joint permitting articulation of said distal phalanx relative to said medial phalanx;
a differential linkage connected to said proximal phalanx and coupling said MCP joint and said PIP joint, said differential linkage adapted for receiving torque from an associated drive output and for transmitting torque from the associated drive output to both said proximal phalanx and medial phalanx, wherein the differential linkage comprises:
a pivot link pivotally connected to said proximal phalanx;
first and second connecting rods pivotally connected to said pivot link, wherein said first connecting rod is located at one end of said pivot link and is adapted for connection to the associated drive output and wherein said second connecting rod is located at another end of said pivot link and is pivotally connected to a primary structural element of said medial phalanx.

7. The apparatus of claim 6, wherein the pivoting differential linkage comprises a compliant spring element pivotally connected to said proximal phalanx for elasticity and shock mitigation.

8. The apparatus of claim 6, further comprising a kinematic linkage operatively coupling said PIP joint and said DIP joint for transmitting torque from the PIP joint to the DIP joint.

9. The apparatus of claim 6, wherein said primary structural element of said medial phalanx to which said second connecting rod is pivotally connected comprises at least one structural plate of the medial phalanx.

10. The apparatus of claim 9, wherein said at least one structural plate of the medial phalanx comprises first and second structural plates.

11. The apparatus of claim 9, wherein said proximal phalanx comprises first and second structural plates between which said pivot link is located and to which said pivot link is pivotally connected.

12. A mechanical finger comprising:
a proximal phalanx and a medial phalanx, the proximal phalanx coupled between a first and a second joint;
the first joint being adapted for coupling to an associated base element to permit articulation of the proximal phalanx with respect to the associated base element;
a differential linkage adapted for receiving torque from an associated drive output and for transmitting torque to both the proximal and medial phalanx, said differential linkage comprising a pivot link pivotally connected to said proximal phalanx;
said differential linkage further comprising first and second connecting rods pivotally connected to said pivot link, wherein said first connecting rod is located at a one end of said pivot link and is adapted for connection to the associated drive output and wherein said second connecting rod is located at another end of said pivot link and is pivotally connected to a primary structural element of said medial phalanx;
wherein said primary structural element of the medial phalanx comprises first and second structural plates, and wherein said second connecting rod is pivotally connected to the first and second structural plates by a pin.

13. A mechanical finger comprising:
a proximal phalanx and a medial phalanx, the proximal phalanx coupled between a first and a second joint;
the first joint being adapted for coupling to an associated base element to permit articulation of the proximal phalanx with respect to the associated base element;
a differential linkage adapted for receiving torque from an associated drive output and for transmitting torque to both the proximal and medial phalanx, said differential linkage comprising a pivot link pivotally connected to said proximal phalanx;
said differential linkage further comprising first and second connecting rods pivotally connected to said pivot link, wherein said first connecting rod is located at a one end of said pivot link and is adapted for connection to the associated drive output and wherein said second connecting rod is located at another end of said pivot link and is pivotally connected to a primary structural element of said medial phalanx;
wherein said primary structural element of said medial phalanx to which said second connecting rod is pivotally connected comprises at least one structural plate of the medial phalanx, and wherein said second connecting rod is pivotally connected to the at least one structural plate by a pin; and,
wherein said proximal phalanx comprises first and second structural plates between which said pivot link is located and to which said pivot link is pivotally connected.

* * * * *